United States Patent [19]

Browne

[11] 4,052,892

[45] Oct. 11, 1977

[54] PRESSURE AND VOLUME RECORDING APPARATUS

[75] Inventor: Lawrence T. Browne, Santa Barbara, Calif.

[73] Assignee: Browne Engineering Corporation, Santa Barbara, Calif.

[21] Appl. No.: 741,810

[22] Filed: Nov. 15, 1976

[51] Int. Cl.² ............................................. G01F 17/00
[52] U.S. Cl. ........................................ 73/149; 73/239; 73/391; 128/2 S; 346/33 TP; 346/129
[58] Field of Search ............ 73/149, 199, 239, 272 A, 73/391, 419; 346/33 TP, 72, 113, 129; 128/2 S, 2.05 D, DIG. 13

[56] References Cited

U.S. PATENT DOCUMENTS

| 845,065 | 2/1907 | Dunn | 346/129 X |
| 3,897,682 | 8/1975 | Brooks | 73/149 |

Primary Examiner—Richard C. Queisser
Assistant Examiner—Charles Gorenstein
Attorney, Agent, or Firm—Donald D. Mon

[57] ABSTRACT

Means for measuring the flow of a stream of fluid and the resistance to said flow. The means can be powered by the fluid whose flow is being measured. First axis motor means moves a chart in response to total flow, and second axis motor means moves marker means on said chart in response to variations in backpressure caused by resistance to flow out of the means. Examples are measuring the muscular response of the urethra and of the bladder.

9 Claims, 4 Drawing Figures

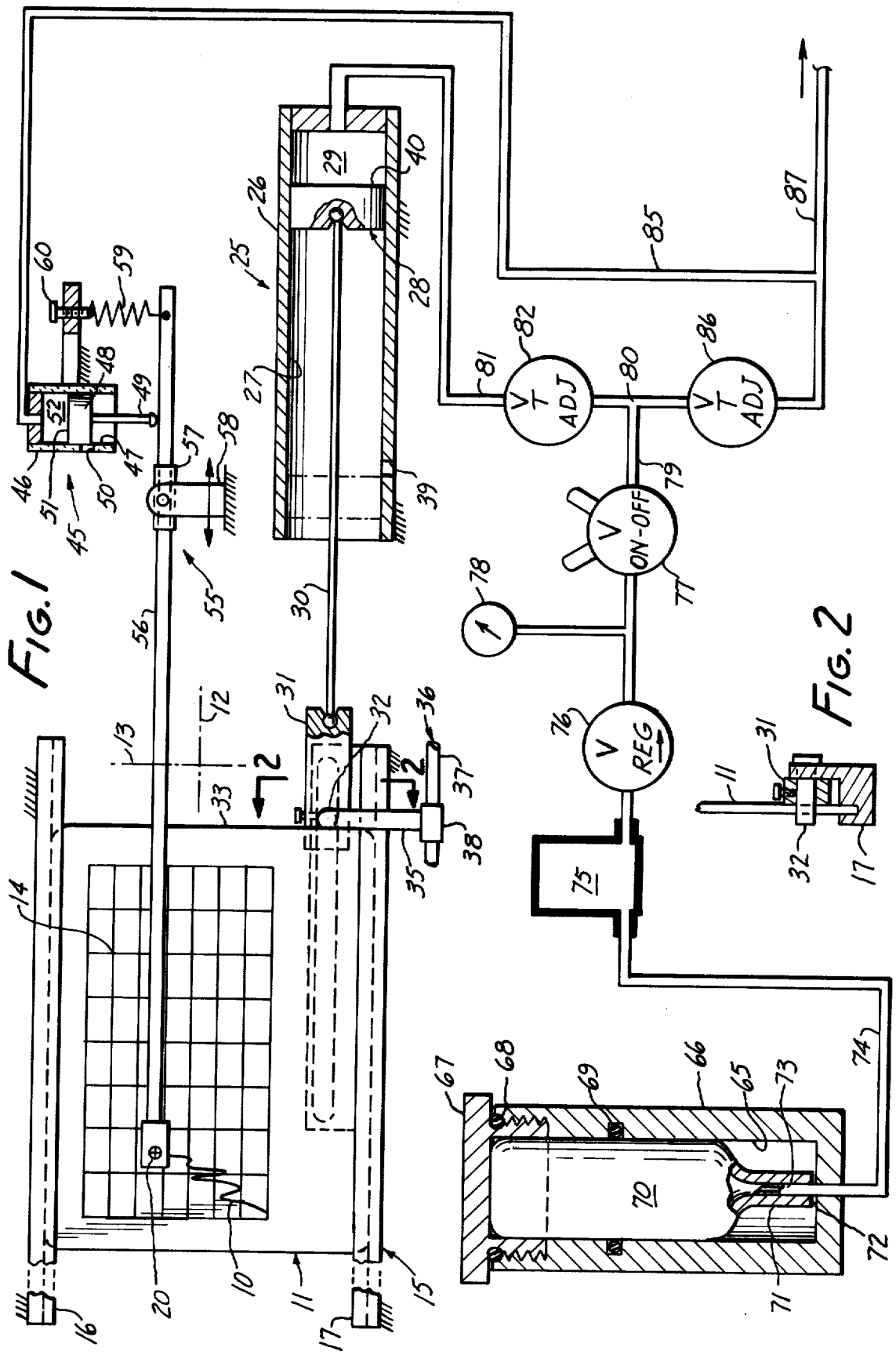

PRESSURE AND VOLUME RECORDING APPARATUS

This invention relates to apparatus for supplying fluid under pressure through a delivery conduit, and providing means to measure and record the total flow and the backpressure resisting said flow. An example is the insufflation of carbon dioxide gas into the urethra and into the bladder of a patient.

The insufflation of gas into cavities for the purpose of investigating the condition of such cavities as the human bladder is well-known. An example of a device for this purpose is shown in Brooks U.S. Pat. No. 3,897,682, issued Aug. 5, 1975. Because the fluids used usually originate from a high-pressure source, and are injected into a region of the human body, it is necessary to assure that the patient is protected against excessive pressure and amounts of fluid. Also, because the apparatus used for these procedures is costly capital equipment, it is desirable for it to be as simple and rugged as possible, so as to present as little risk of malfunction or need for servicing as possible.

Because this apparatus is used in and around the human body, it is advantageous for it to be powered by pressure of the dispensed fluid. Then there is no electrical risk. It is useful for it to be self-contained and powered by pressure of the fluid.

It is an object of this invention to provide apparatus for supplying fluid under pressure at sensibly constant rates of flow wherein there is obtained a measurement and chart recording of total volume of fluid delivered to the patient, and simultaneous resistance to the entry of the fluid itself is used to power the apparatus.

It is another object of this invention to provide limiting means which prevents the device from applying excessive pressure, or from injecting excessive quantities of fluid into the patient.

Apparatus according to this invention includes pressure-regulated fluid supply means, and a chart recorder comprising a first axis drive motor and a second axis drive motor, these motors being actuable by fluid under pressure. A first axis conduit and a second axis conduit interconnect said first and second axis drive motors, respectively, to said supply means. A first axis restrictor and a second axis restrictor are placed in the respective first and second axis conduits between the respective motors and supply means.

Chart support means is provided for supporting a chart for movement along said first axis. Said first axis drive motor moves the chart and support means relative to one another. Marker support means is provided for holding a marker against the chart. The second axis drive motor moves the marker and the chart relative to one another. A delivery conduit is connected to the second axis conduit. The first axis drive motor operates unidirectionally in response to fluid delivered to it, and the second axis drive motor operates bi-directionally in response to pressure in the second axis conduit downstream from its respective restrictor.

According to a preferred but optional feature of the invention, the pressure-regulated fluid supply means comprises a relatively high pressure gas source with a regulator valve adapted to deliver fluid at a predetermined pressure.

According to another preferred but optional feature of the invention, the motors are piston-cylinder assemblies in which a vent port is provided in the cylinder wall to vent cylinder pressure at a selected point in the travel of the piston, whereby in one situation to limit the total volume of fluid which can be delivered, and in another situation to limit the maximum pressure which can be exerted.

According to still another preferred but optional feature of the invention, the marker support means comprises a pivoted spring-loaded arm, and in which the second axis motor is a piston-cylinder assembly, the arm being biased to oppose the pressure in the second axis conduit.

The above and other features of this invention will be fully understood from the following detailed description and the accompanying drawings, in which:

FIG. 1 is a schematic drawing, partly in cutaway cross-section, showing the presently-preferred embodiment of the invention;

FIG. 2 is a fragmentary cross-section taken at line 2—2 of FIG. 1; and

Figure 3:
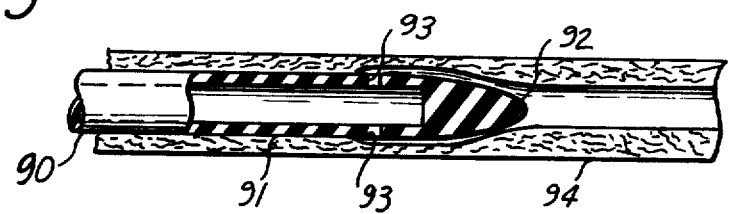
FIGS. 3 and 4 are fragmentary axial cross-sections showing two types of catheters used in two diagnostic procedures utilizing the apparatus of this invention.
Figure 4:
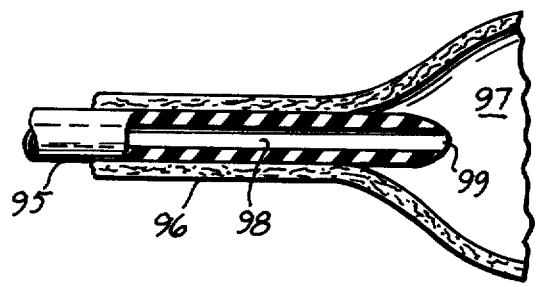

The ultimate objective of this invention is to draw a graph line 10 on a chart 11 to record an accumulated (total) delivered volume of fluid through, and the simultaneous pressure in, a delivery conduit from which the fluid exits to the patient. The graph has a first axis 12 and a second axis 13. In FIG. 1, first axis 12 is for the total volume of fluid delivered. The second axis is for the simultaneous pressure in the delivery conduit. A typical rectangular coodinate system 14 is printed on the chart, divided into appropriate units.

Chart support means 15 comprises a pair of tracks 16, 17. The chart, or a device supporting the chart, travels to the right or left along first axis 12. Marker means 20, such as a recording pen, is brought against the chart to draw the graph line.

A first axis motor 25 comprises a piston-cylinder assembly which includes a cylinder 26 having a circularly cylindrical bore 27 within which a circularly cylindrical piston 28 is reciprocably fitted. The piston and the wall of bore 27 make a close, fluid-sealing sliding fit with one another. Fluid pressure in chamber 29 tends to enlarge chamber 29 and move piston 28 to the left. Connecting rod 30 is connected to piston 28 and to a slide member 31 which is slidably mounted to track 17.

Slide member 31 carries a stud 32 which abuts against the right-hand edge 33 of chart 11. The connecting rod, slide member, and stud constitute means whereby the first axis drive motor is enabled to move the chart to the left in FIG. 1 relative to the support means.

A link 35 may be connected between the stud and a catheter 37, or some other device whose position relative to some datum location is desired to be known. Such a catheter might, for example, be the output point for a fluid to be delivered by this apparatus. The link may be attached to the catheter by a clamp 38. The catheters and procedures involved will more fully be disclosed below.

A vent port in the form of a groove 39 is cut through the wall of cylinder 26. When the right-hand face 40 of the piston passes the right-hand edge of vent groove 39, pressure will be dumped from chamber 29, and the chart movement will stop. This will soon stop delivery of fluid, as will more fully be discussed below.

In operation, the first axis motor is unidirectionally driven. It can be restored to a starting position by manually pushing the chart or the 1 ink 35 to the right in FIG. 1 while chamber 29 is connected to atmosphere.

Second axis motor 45 also comprises a piston-cylinder assembly. It includes a cylinder 46 having a bore 47 in which a piston 48 makes a close, fluid-sealing, sliding fit. It can reciprocate axially in the cylinder and includes a push rod 49 which projects beyond the open end of the cylinder. A vent port in the form of a groove 50 is cut through the wall of the cylinder so that when face 51 of the piston passes the edge of the groove, pressure will be vented to atmosphere from chamber 52. This constitutes a safety limit for the maximum pressure which can be applied to the patient.

Marker support means 55 comprises a pivoted arm 56. It may conveniently be supported in a pivoted sleeve 57. Sleeve 57 is pivoted to a block 58. The location of the block along the length of the pivoted arm is adjustable. This adjusts the range of the left-hand end of the pivoted arm to which the marker is attached. This provides for a multi-range read-out, because the same deflection of the end of the arm can be made to read out different selected pressures.

The push rod 49 presses downwardly against the right-hand portion of the arm. Its downward pressure is opposed by a bias spring 59. Spring 59 is a tension spring connected to an attachment 60 that is fixed relative to the frame of the machine or relative to the cylinder 46, and to the right-hand portion of the pivoted arm. Attachment 60 is a screw which can be turned to adjust the tension of the bias spring. Therefore, the position of the arm will also be determined by the interaction between bias spring 59 and the pressure in chamber 52. Tension on the spring can also be adjusted to determine the pressure range, and will more usually be the means to secure this objective.

The instantaneous pressure will be recorded as a function of the vertical position of the marker on the chart, which is set by the second motor. The accumulated total volume passed from the start of the procedure to the moment of recording at which the said pressure exists will be determined by the position of the chart relative to its support as set by the first motor. The term "motor" is used in this specification in its broadest sense. Motive means other than piston-cylinder assemblies can be used instead, positivedisplacement vane-type and gear type rotary motors, for example. Piston-cylinder assemblies are the least complicated.

Because the pressures utilized in this system are relatively low, and the pressure differentials measured are small portions of it, it is important to have as little frictional loss in the system as possible. For example, a delivered pressure will often approximate 8 psi, and backpressure differentials to be measured will be on the order of 0.13 psi. A suitable low friction motor can be made from an accurately cylindrical and smooth glass cylinder, and an accurately cylindrical and smooth graphite piston. These make a very satisfactory fluid seal with one another, and yet have only negligible sliding friction losses between them.

The foregoing describes the mechanical features of the invention. The fluid flow features will now be described.

A receiver 65 comprises a strong-walled vessel 66 having a removable pressure-tight cap 67 with seals 68, 69. It receives a typical carbon dioxide pressure cartridge 70. Such cartridges have a neck 71 with a tip 72 which is penetrable by a needle 73 to release gas. It is usual for the initial pressure in such a gas cartridge to be on the order of 900 psi. When released, the gas flows through a pressure line 74 to a tank 75 which, although shown smaller on the drawings for convenience in illustration, will usually be about 9 to 10 times the volume of the cartridge, whereby to reduce the maximum pressure in the system to about 100 psi.

A pressure regulator valve 76 receives gas from the tank and supplies it at adjustably regulated pressure to an off-on valve 77. This is usually about 8 psi. A flow rate gauge 78 is teed into line 79 downstream from the pressure regulator to indicate the approximate gas flow rate. It may simply be a pressure gauge calibrated to indicate rate. The off-on valve 77, when open, delivers fluid at the predetermined regulated pressure. The apparatus upstream from, and including valve 77, is sometimes referred to as a "pressure-regulated fluid supply means". It delivers fluid to a tee 80.

A first axis conduit 81 connects the pressure regulated fluid supply means to chamber 29 of first axis motor 25. An adjustable first axis orifice 82, such as an adjustable needle (throttle) valve, is connected in the first axis conduit between the fluid supply and the first axis conduit between the fluid supply and the first axis motor.

A second axis conduit 85 connects the pressure regulated fluid supply means to chamber 52 of second axis motor 45. A second axis adjustable orifice 86, again such as an adjustable needle (throttle) valve, is connected in the second axis conduit between the fluid supply and the second axis motor. The orifices are connected to one another. A delivery conduit 87 tees off from the second axis conduit to convey the gas to a point of use which might, for example, be a catheter 37.

The operation of this device will now be described. In understanding this invention it is important to bear in mind that the pressures used are guite low, and that the variations in the pressure caused by the back forces exerted by the urethra and the bladder are relatively small percentages of already small pressures. Accordingly, everything is operating relatively close to ambient pressures.

The cartridge is placed in the receiver. The pressure-tight cap is placed over its opening and is then screwed down in place. This forces the cartridge down onto the needle so the needle penetrates it and releases the gas into the needle. Seals 68, 69 are located so that this operation takes place without loss of gas from the receiver. Seal 69 makes a peripheral contact with the outer wall of the cartridge at all times when the gas is released.

The off-on valve is initially closed, and pressure in the tank rises to whatever value is determined by the relative volumes between the cartridge and the tank and the original cartridge pressure. The regulator valve is set to deliver gas at a predetermined, selected, pressure.

The settings of the two orifices ("restrictors") are adjusted so as to give the desired movement of the first axis motor relative to the volume delivered to the delivery conduit. This constitutes a splitting of flow from the source into two independent streams. In the stream which includes second axis conduit 85 and delivery conduit 87, the major portion flows through the delivery conduit. The rest of it flows into the second axis conduit 85. The second axis conduit is more of a signal line than a delivery line and uses ony negligible quantity of gas compared to the amount which flows through the delivery conduit.

The first axis motor actually operates as an accumulator, and, as the gas enters this mechanism, the piston moves along its cylinder in a direct, nearly linear, relationship to the quantity of gas which is fed to this motor, because there is so little friction involved. The ratio of the gas flows between that which passes through the first axis conduit and that which passes out the delivery conduit has been been established by the adjustment of the orifices. This relationship, once set, will remain constant. Therefore the flow into the first axis motor will be directly proportional to the flow through the delivery conduit, within reasonable limits and to a reasonable degree of accuracy.

As the volume delivered increases, the piston of the first axis motor moves to the left in FIG. 1, moving the chart along its tracks, the distance moved being a function of and substantially directly proportional to the quantity of gas which has flowed out the delivery conduit. By adjusting the relative flows of the gas streams with the orifices, a wide range of total volumes can accurately be measured and recorded. Because there is so little friction loss in the motor employed, the tendency of the first motor is to drive the chart until the pressure chamber 29 has dropped nearly to atmospheric.

If desired, means such as the catheter can be connected to the stud as shown and be moved with and by it. The chart will then also indicate the location of a catheter in a urethra, for example, at the time a volume had been delivered. The pressure at that time and location can also be read out. This can have important diagnostic values.

The second axis motor is powered by the pressure downstream from the second orifice. This motor also is a low-friction type motor, which is desirable because it is intended to be responsive to relatively low pressure differentials. The spring bias force and the ratio of the portions of the arm of each side of the pivot are first set. This enables a wide range of marker movements relative to pressures being measured.

It is convenient for the axial location of the cylinder of each motor to be linearly adjustable. Means (not shown) can be provided for that purpose. This device can measure and record pressures down to a low-end capability of perhaps 1 to 2 cm. of water pressure. The adjustable bias means and the movable pivot axis permit the adjustment of the zero point and its range and its linearity.

It sill now be seen that when the off-on valve is turned on, pressure will flow from the supply means so as to move the chart and the marker in synchronism with one another to indicate the backpressure of the system and the total volume delivered by the system. This has important diagnostic implications, especially in the field of urology.

The above system is intended to be used primarily for making two types of measurements when a catheter is used for the delivery tube. The first is to secure a pressure vs. distance urethral pressure profile. This is acomplished with the use of a catheter 90 which has a continuous peripheral wall 91, a closed end 92 and a side wall ports 93. It is inserted into a urethra 94 which is shown schematically, in the direction of the bladder, the bladder lying to the right in FIG. 3. It is of interest to urologists to know the force with which the wall of the urethra clamps down upon the catheter. The pressure regulated fluid supply, while it discharges fluid at a constant pressure, does so at a pressure which is sufficiently high that it can overcome the resistance of the urethral wall, and accordingly approaches the capacity of a constant delivery pump. This is to say that the device will deliver fluid to the urethra at a substantially constant rate regardless of the resistance to it, on the asssumption that the resistance to it is a relatively small percentage of the total pressure. In fact, the range of pressures in low range is usually between only about 0—75 centimeters of water pressure and in the high range between zero and about 150 centimeters of water. A total volume to be delivered will rarely exceed 500 cubic centimeters. Accordingly, as the catheter at the side wall ports is surrounded by a strong urethral wall, the backpressure (pressure in the catheter) will increase, and when the wall is relatively weaker it will decrease. It decreases because there is less resistance to the discharge at the side wall ports. The presssure profile, knowing the distance of insertion into the urethra is a profile reading of the condition of the urethra at every point along its length.

Another diagnostic procedure of importance is called a cystometrogram, in which the resistance by the bladder to insertion of fluid therein is measured. The bladder is rather like a loose sack and exerts only mild resistance to addition of liquid until it nears its capacity at which time its resistance is quite large. However, even the mild resistance is of interest. A catheter 95 is inserted through urethra 96 into bladder 97. This catheter has a central passage 98 with an open end 99. The "backpressure" will measure whatever resistance the bladder makes to the entry of the fluid, especially as the musculature comes into operation when the bladder nears capacity. A diagram showing the condition of pressure vs. volume of fluid in the bladder is of great diagnostic value to the physician.

It will also be noted that the entire device operates from the pressure of the fluid itself. There need be no external power supplies, and the patient is thereby protected from the risk of exposure to electrical circuits.

The term "fluid" has been used herein to mean either a liquid or a gas. It is evident that the same features which are effective with gas are also effective with a liquid. However, generally speaking, this will be used for delivery of gas more frequently than for liquids, although both are intended to be within the scope of this invention. When liquids are delivered, a suitable pressurized source is provided.

It is possible to provide bleed means (not shown) quickly to dump the pressure downstream from the off-on valve when this valve is turned off. However, ordinarily the pressure in the system will simply dissipate through the delivery tube quickly enough for most practical purposes.

The safety feature of the vent ports in the two motors is emphasized. In the first axis motor, when the piston passes and opens the vent port, chart movement will stop, and system pressure will be bled off. Although this is not an instantaneous stop, because the vent port is downstream from one of the throttle valves, still there is no resistance to flow to atmosphere, and it will bleed the system down at a suitable rate, thereby limiting the amount of fluid which can be injected into the patient. In the second axis motor, when the piston uncovers the respective vent port, there is a quick reduction in pressure, and the patient is thereby protected against excessive pressure.

This apparatus is inherently fail-safe, protects the patient from the risk of over-supply and excessive pressure, and provides a device which is powered merely by the pressure of the fluid being dispensed.

This invention is not to be limited by the embodiment shown in the drawings and described in the description, which is given by way of example and not of limitation, but only in accordance with the scope of the appended claims.

I claim:

1. Apparatus for supplying a flow of fluid under pressure to a delivery conduit, and measuring the total volume of fluid passed by the delivery conduit and also the resistance to the discharge of said flow from the delivery conduit, said apparatus comprising: pressure-regulated fluid supply means; chart recorder means comprising a first axis drive motor, and a second axis drive motor, said motors being actuable by fluid under pressure; a first axis conduit and a second axis conduit connecting the respective first and second drive motors to said fluid supply means; a first axis restrictor and a second axis restrictor in the respective first and second axis conduits between the respective motor and the fluid supply means, chart support means for supporting a chart for movement along said first axis, said first axis drive motor being adapted to move the chart and said chart support means relative to one another, marker support means for holding a marker against the chart, said second axis drive motor connected to said marker support means to move the marker and the chart relative to one another, said delivery conduit interconnected to said second axis conduit, said first axis drive motor operating unidirectionally in response to fluid delivered to it, and said second axis drive motor operating bi-directionally in response to pressure in said second axis conduit.

2. Apparatus according to claim 1 in which said pressure-regulated fluid supply means comprises a source of fluid, and a pressure-regulator valve which discharges gas at a predetermined pressure.

3. Apparatus according to claim 2 in which said fluid supply means further includes a tank to receive gas under pressure at a lower pressure than the source of said gas.

4. Apparatus according to claim 3 in which said source is a gas cartridge, and in which the tank has a larger volume than the cartridge.

5. Apparatus according to claim 1 in which each motor comprises a piston and a cylinder.

6. Apparatus according to claim 5 in which the first axis motor has a vent port in its cylinder to vent fluid which drives the respective piston to limit the axial travel of the piston after the piston passes the vent port.

7. Apparatus according to claim 5 in which the second axis motor has a vent port in its cylinder to vent pressure which drives the respective piston in its increasing-pressure direction to vent the fluid in the second axis conduit when it exceeds a predetermined pressure.

8. Apparatus according to claim 1 in which the marker support means comprises an arm which is bi-directionally driven by the second axis drive motor.

9. Apparatus according to claim 5 in which the cylinders are made of glass, and the pistons are made of graphite.

* * * * *